United States Patent

O'Rourke

[11] Patent Number: 5,882,311
[45] Date of Patent: Mar. 16, 1999

[54] CALIBRATION FOR BLOOD PRESSURE PULSES

[75] Inventor: Michael Francis O'Rourke, Hunters Hill, Australia

[73] Assignee: PWV Medical Pty Ltd., Ermington, Australia

[21] Appl. No.: 973,247
[22] PCT Filed: Jun. 5, 1996
[86] PCT No.: PCT/AU96/00340
  § 371 Date: Apr. 6, 1998
  § 102(e) Date: Apr. 6, 1998
[87] PCT Pub. No.: WO96/39074
  PCT Pub. Date: Dec. 12, 1996

[30] Foreign Application Priority Data

Jun. 5, 1995 [AU] Australia ............... PN3383

[51] Int. Cl.⁶ ......................... A61B 5/00
[52] U.S. Cl. .................. 600/485; 600/490; 600/500
[58] Field of Search ................... 600/485, 490, 600/493–6, 500

[56] References Cited

U.S. PATENT DOCUMENTS

| | | | |
|---|---|---|---|
| 4,873,987 | 10/1989 | Djordjevich et al. | 128/672 |
| 4,907,596 | 3/1990 | Schmid et al. | 600/485 |
| 5,101,828 | 4/1992 | Welkowitz et al. | 128/668 |
| 5,241,964 | 9/1993 | McQuilkin | 600/385 |
| 5,269,310 | 12/1993 | Jones et al. | 600/485 |
| 5,746,698 | 5/1998 | Bos et al. | 600/493 |
| 5,785,659 | 7/1998 | Caro et al. | 600/500 |

FOREIGN PATENT DOCUMENTS

| | | |
|---|---|---|
| 0 297 146 A1 | 1/1989 | European Pat. Off. . |
| WO 90/11043 | 10/1990 | WIPO . |
| WO 95/18564 | 7/1995 | WIPO . |

Primary Examiner—Robert L. Nasser
Attorney, Agent, or Firm—Baker & Daniels

[57] ABSTRACT

Disclosed is an improved arrangement for allowing more accurate automatic calibration for a system in which blood pressure pulses are derived for remote sites from a calibrated measurement and a waveform measurement, when these are made at different sites. Where a calibrated measurement is made, say, at the brachial artery (11), and a waveform recorded at the radial artery (12), a waveform is derived for the calibrated site using a known transfer function, this drived waveform is then calibrated by the measurements already made, and the calibrated waveform for any remote site, for example the ascending aorta (14), can be derived using a known transfer function.

13 Claims, 2 Drawing Sheets

Ascending Aorta   Brachial Artery   Radial Artery

Brachial artery to ascending aorta

Radial artery to ascending aorta

CALIBRATION FOR BLOOD PRESSURE PULSES

TECHNICAL FIELD

The present invention relates to the measurement of peripheral blood pressure pulse waveforms and the use of these waveforms to determine pulse waveforms at other sites. More particular, it is concerned with the calibration of these waveforms.

BACKGROUND ART

A technique for utilising peripheral pressure pulses to determine the pulse waveform at other body sites, particularly the ascending aortic waveform, is disclosed in U.S. Pat. No. 5,265,011 by Michael F. O'Rourke. The books "The Arterial Pulse" by O'Rourke, Kelly and Avolio published by Lea Febiger, Philadelphia USA 1992 and "Arterial Vasodilation", by O'Rourke, Saffer, and Dzau, published by Arnold, London 1993 disclose the use of a measured peripheral waveform to determine the waveform at another site, using an empirically determined transfer function. The derived waveform can be calibrated, as it is derived from the peripheral waveform which itself is calibrated. In these documents, it is assumed that the brachial cuff sphygmomanometer measurement can be used to directly calibrate waveforms measured at the radial artery. It is assumed that relatively little change occurs in the parameters between the brachial artery and the radial artery. Whilst this is a reasonable working assumption, it is not strictly accurate.

It is an object of the present invention to provide an improved calibration procedure, such that derived waveforms are able to be more accurately calibrated.

SUMMARY OF INVENTION

According to a first aspect, the present invention provides a method of calibrating a derived pressure pulse waveform, said derived waveform being determined by processing a peripherally measured waveform, comprising the steps of:

1. measuring at a first site a blood pressure pulse waveform;

2. measuring substantially simultaneously using a calibrated instrument the systolic and diastolic pressures at a second site;

3. determining the pulse waveform shape at said second site from the waveform measured at said first site using a first predetermined transfer function;

4. calibrating the waveform at said second site using the measured systolic and diastolic pressures;

5. determining the pulse waveform shape at a third site directly or indirectly from the waveform measured at said first site using a second predetermined transfer function;

6. calibrating the waveform at said third site directly or indirectly from the calibrated waveform from said second site.

Preferably, the measurements at the first and second sites are performed non-invasively. The first site may be, conveniently, the radial artery or the finger, and the second site may be the brachial artery, although any convenient site may be chosen.

It will be appreciated that the present invention is not limited to the steps being performed in the particular order shown above. The three different transfer functions mentioned above may in fact be only two different transfer functions, depending upon how the calculation is desired to be performed. The user is only required, in any case, to measure the waveform, and make a calibration measurement. For example, the measured waveform at the first site may be used to derive an uncalibrated waveform at the second site, which is then calibrated by measurement at that site. The calibrated waveform may then be used to calibrate the waveform at the first site. From the calibrated second site waveform, a calibrated waveform at the third site can be directly obtained by applying the appropriate transfer function.

It will be understood that the calculation process may actually be performed in a number of equivalent ways. However, the general principle of the present invention is retained—that is, that a measurement at one site is used to provide calibration for the derived waveform, and at a second site a waveform is acquired for calculating the derived waveform, with different transfer functions being used between the first and second sites to the site for which the derived waveform is required.

The measurement steps may be performed with manually operated instruments, and the output data processed by any suitable processor, or the waveform may be measured continuously and calibrated periodically or in real time, either manually or automatically.

This approach allows for a convenient waveform measurement site to be used, which may not be reliable or convenient in terms of accuracy of calibrated pressure measurements, with calibration performed at a convenient site for calibrated measurement.

BRIEF DESCRIPTION OF DRAWINGS

The present invention will now be described with reference to the accompanying figures, in which.

DESCRIPTION OF EMBODIMENT

It will be appreciated that while the present invention is described with reference to particular sites for pressure measurement and for which pressures are derived, the inventive principle is equally applicable to other sites. Moreover, whilst the use of non-invasive techniques is presently preferred for practical reasons, the present invention contemplates the use of an invasively derived waveform or calibration if available or desired. The inventive method may be incorporated in software in any suitable digital processing device, of the type disclosed in the references cited above, as would be readily understood by those skilled in the art.

Figure 1:
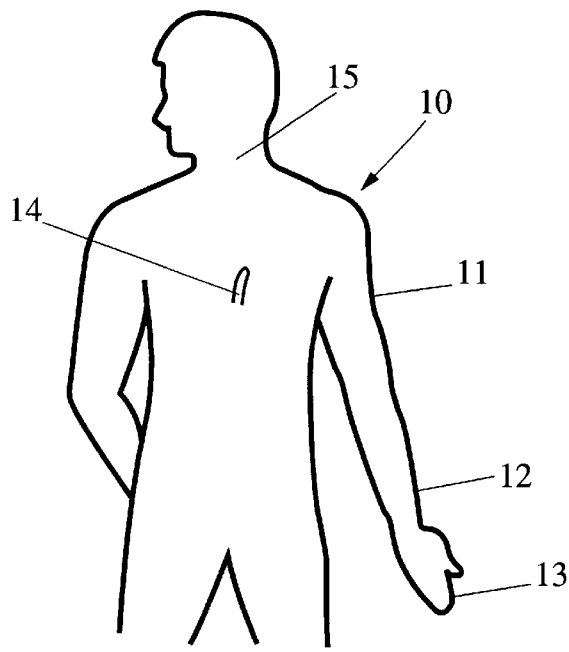
FIG. 1 is a schematic diagram illustrating the sites where measured and derived pressures are located.

Referring to FIG. 1, this is a schematic illustration of the pressure measurement sites used according to the following discussion. Three sites are of relevance to this discussion on person 10. The site for which the calibrated pressure waveform is required is illustratively the ascending aorta 14. It will be appreciated that according to the present invention this could be any other site for which suitable transfer functions have been derived, for example, the carotid artery 15. The calibrated measurement may be derived by conventional sphygmomanometry at the brachial artery 11. The waveform may be acquired for the purposes of this example at the radial artery 12—however, it will be appreciated that other sites may be used, for example the finger 13, or carotid artery 15. An uncalibrated waveform may even be acquired at the site for which a calibrated waveform is required, if this is accessible to the pressure measurement instrument.

The waveform may be acquired using any suitable means—for example, a tonometer, or at the finger using the FINIPRES device, or by an in-dwelling pressure catheter. Such devices are widely available commercially, and the reader will be familiar with their operation. The process of acquiring a waveform using a tonometer is described in the O'Rourke et al references cited above. Similarly, the general principles of deriving a waveform for the ascending aorta using transfer functions, and the techniques for deriving such transfer functions, are described in those documents, which are hereby incorporated by reference. Various transfer functions have been published in the scientific literature, which could be adopted for use in the present invention. It will be appreciated that the transfer functions may be derived on a different basis, if desired.

Figure 2:
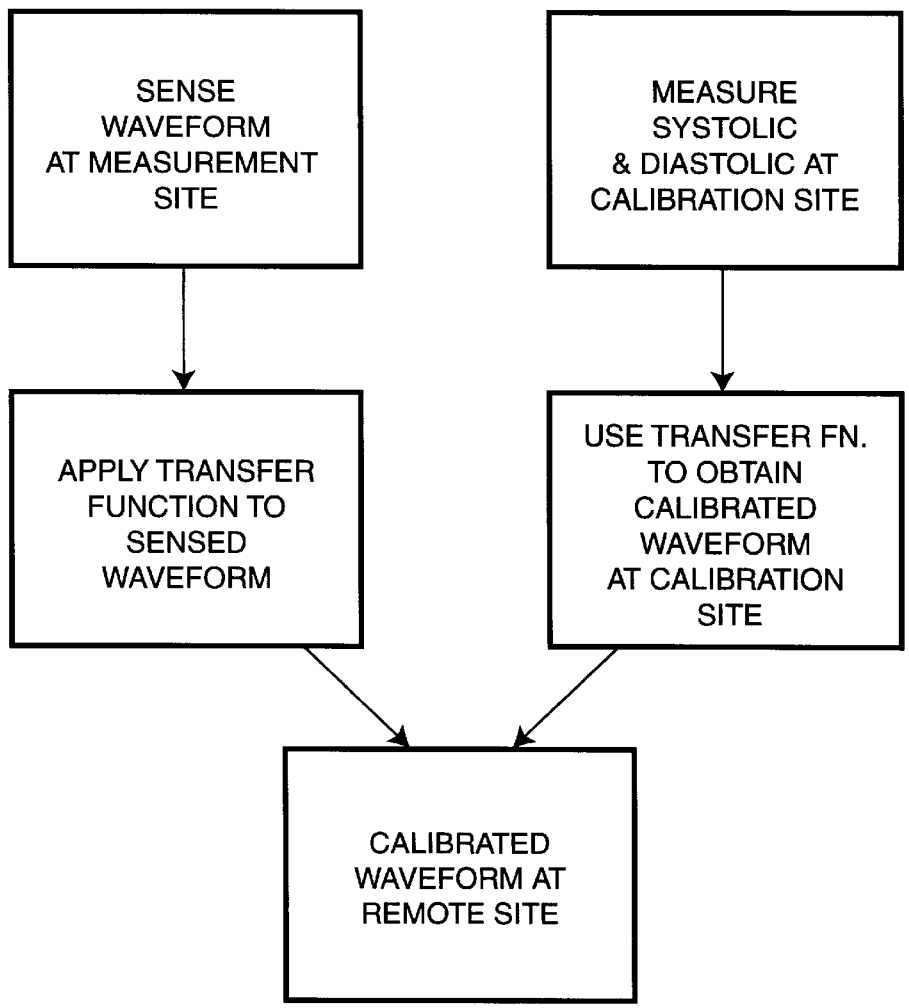
FIG. 2 is a flow chart illustrating the determination of the remote site pressure waveform.
Figure 3:
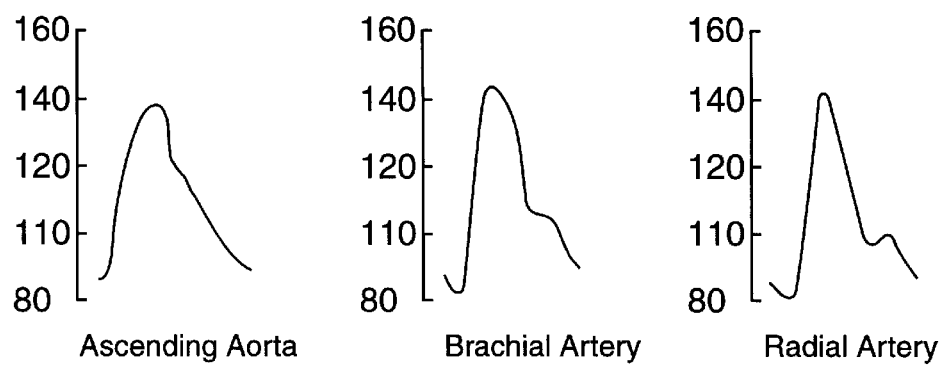
FIG. 3 is an illustration showing typical pressure waveforms for the ascending aorta, brachial artery and radial artery.
Figure 4:
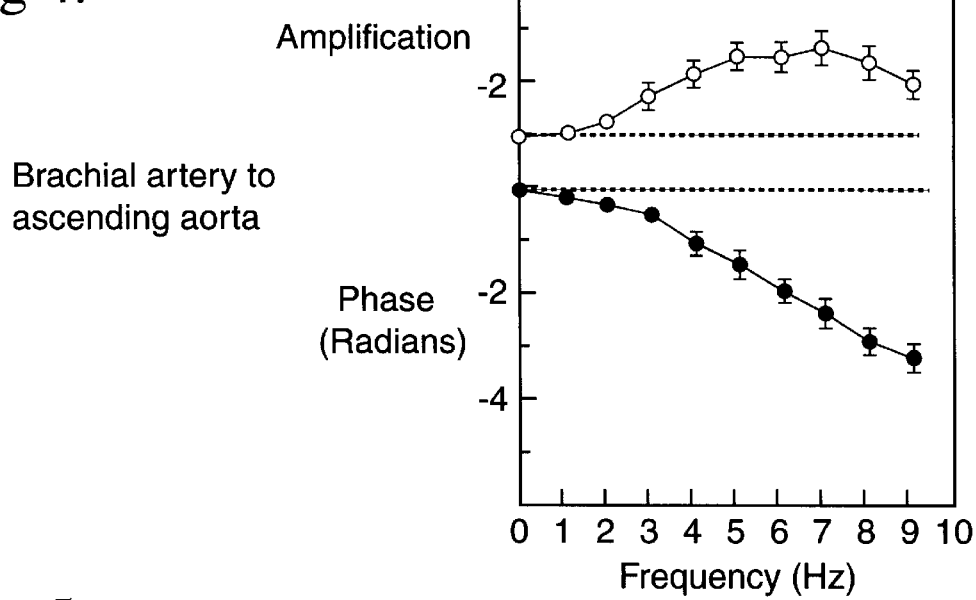
FIGS. 4 & 5 are graphs showing the transfer functions between the brachial artery and the ascending aorta, and between the radial artery and the ascending aorta.
Figure 5:
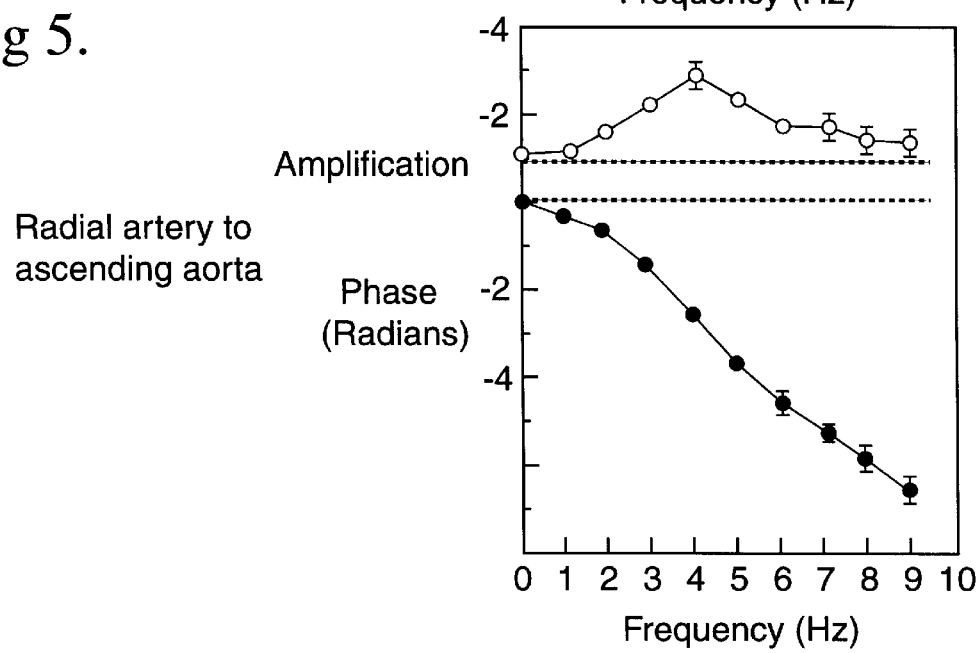

FIG. 2 illustrates the process according to the present invention. The waveform is measured at, for example, the radial artery, and the known transfer function used to derive the shape of the waveform at the ascending aorta. A suitable transfer function is shown in FIGS. 4 & 5 between each of the brachial and radial artery, and the ascending aorta. FIG. 3 illustrates typical pressure waveforms at the radial artery, brachial artery and ascending aorta.

At the same time, or shortly before or after, conventional sphygmomanometry may be used to measure the systolic and diastolic pressures at a suitable site, for example at the brachial artery. The transfer function defines a relationship between the relative waveform magnitudes at the different sites related by the function. From the radial artery waveform, a transfer function can be used to derive an uncalibrated waveform at the brachial artery, which can then be calibrated using the measured systolic and diastolic pressures at that site. The ascending aorta waveform can then be calibrated from the relative magnitude of the waveforms at the ascending aorta and the brachial artery, and the known calibration at the brachial artery. Accordingly, the derived ascending aorta pressure waveform can be calibrated. It will be appreciated that the processing using transfer functions is conveniently carried out using the Fourier transform of the waveforms, using a suitably programmed microprocessor.

It will be appreciated that an alternative calculation process could be used. For example, the transfer function between the brachial artery and the radial artery could be used to determine a calibrated radial pressure waveform, and the transfer function to the ascending aorta used to determine the calibrated ascending aorta waveform from the radial waveform.

Another alternative would be to use a transfer function from the calibrated brachial artery waveform to derive the calibrated ascending aorta pressure waveform using the appropriate transfer function. The calculation could also be performed in real time, subject to a suitable processor and software being employed, as would be apparent to those skilled in the art. The basic technique remains the same.

It will be appreciated that the present technique allows for a calibrated waveform to be derived for any selected site, from a waveform measured at a different site, provided the corresponding transfer function is known.

The reader will appreciate that variations and additions are possible within the spirit and scope of the invention, within the general inventive concept.

I claim:

1. A method of calibrating a derived pressure pulse waveform, said derived waveform being determined by processing a peripherally measured waveform, comprising the steps of:
    a. measuring at a first site a blood pressure pulse waveform;
    b. measuring substantially simultaneously using a calibrated instrument the systolic and diastolic pressures at a second site;
    c. determining the pulse waveform shape at said second site from the waveform measured at said first site using a first predetermined transfer function;
    d. calibrating the pulse waveform shape at said second site using the measured systolic and diastolic pressures to provide a calibrated waveform;
    e. determining the pulse waveform shape at a third site directly or indirectly from the waveform measured at said first site using a second predetermined transfer function;
    f. calibrating the waveform at said third site from the calibrated waveform from said second site, so that a calibrated waveform is derived from said third site.

2. A method according to claim 1, wherein said step f. includes deriving the calibrated waveform at said third site by applying said second transfer function to the calibrated waveform at said second site.

3. A method according to claim 2, wherein steps c. to f. are performed by software.

4. A method according to claim 2, wherein the first site is selected from the group comprising the radial artery and the finger, and the second site is the brachial artery.

5. A method according to claim 1, wherein said step e. includes calibrating the measured waveform at said first site from the calibrated waveform at said second site, and deriving said third site waveform by applying a said second transfer function from said calibrated waveform at said first site to said third site.

6. A method according to claim 1, wherein the first site is selected from the group comprising the radial artery and the finger, and the second site is the brachial artery.

7. A method according to claim 1, wherein steps 3 to 6 are performed by software.

8. A method according to claim 5, wherein steps c. to f. are performed by software.

9. A method according to claim 5, wherein the first site is selected from the group comprising the radial artery and the finger, and the second site is the brachial artery.

10. A method according to claim 1, wherein the first site is the same as the third site.

11. A method according to claim 1, wherein said step f. includes deriving the calibrated waveform at said third site by applying a third transfer function to the calibrated waveform from said second site.

12. A method according to claim 1, wherein said step f. includes deriving the calibrated waveform at said third site by applying a third transfer function to the waveform measured at said first site.

13. A method according to claim 1, wherein said step f. includes deriving the calibrated waveform at said third site by applying a third transfer function to the pulse waveform shape from said second site.

* * * * *